United States Patent [19]

Lafon

[11] 4,128,656
[45] Dec. 5, 1978

[54] PIPERONYLAMINE DERIVATIVES

[75] Inventor: Louis Lafon, Paris, France

[73] Assignee: Societe Anonyme Dite: Laboratoire L. Lafon, Maisons Alfort, France

[21] Appl. No.: 779,585

[22] Filed: Mar. 21, 1977

[30] Foreign Application Priority Data

Mar. 23, 1976 [GB] United Kingdom ............... 11709/76

[51] Int. Cl.$^2$ .............................................. A61K 31/36
[52] U.S. Cl. ................................ 424/282; 260/326 R; 260/340.5 R
[58] Field of Search .................. 260/340.5 R; 424/282

[56] References Cited

U.S. PATENT DOCUMENTS

| | | | |
|---|---|---|---|
| 2,578,696 | 12/1961 | Gump et al. | 260/340.5 R |
| 3,201,470 | 8/1965 | Huebner | 260/340.5 R |
| 3,471,522 | 10/1969 | Biel et al. | 260/340.5 R |
| 3,523,954 | 8/1970 | Koppe et al. | 260/340.5 R |
| 3,532,749 | 10/1970 | Biel et al. | 260/340.5 X |

Primary Examiner—Ethel G. Love
Attorney, Agent, or Firm—Poms, Smith, Lande & Glenny

[57] ABSTRACT

N-propargyl-piperonylamine of the structural formula:

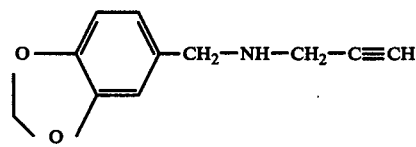

and its addition salts are useful in reducing appetite, fatigue, and aggression.

2 Claims, No Drawings

PIPERONYLAMINE DERIVATIVES

The present invention provides N-propargyl-piperonylamine of the formula:

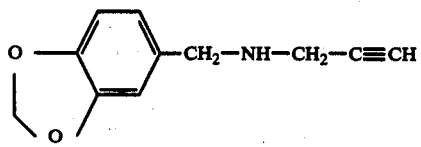
(I)

and its addition salts. By addition salts are meant the addition salts with acids obtained by reaction of the free base with an inorganic or organic acid. Suitable acids include hydrochloric acid, hydrobromic acid, sulphuric acid, phosphoric acid, nitric acid, formic acid, acetic acid, oxalic acid, fumaric acid, maleic acid, malic acid, citric acid, tartaric acid, ascorbic acid, glutamic acid, aspartic acid, methanesulphonic acid, p-toluenesulphonic acid and succinic acid.

N-Propargyl-piperonylamine can be prepared by reacting 3,4-methylenedioxy-benzylamine with a propargyl halide of the formula Hal—CH$_2$—C≡CH, where Hal is I, Br, Cl or F, bromine being preferred, and, optionally converting the base thus obtained into an addition salt.

The total synthesis of the product of the formula I is summarized below:

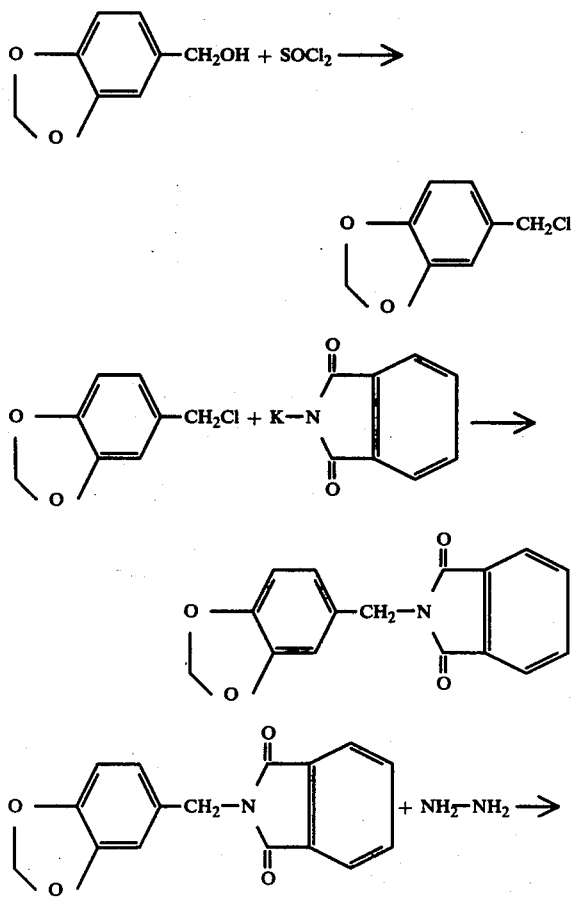

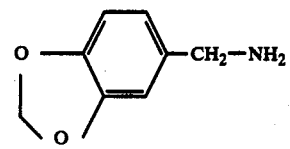

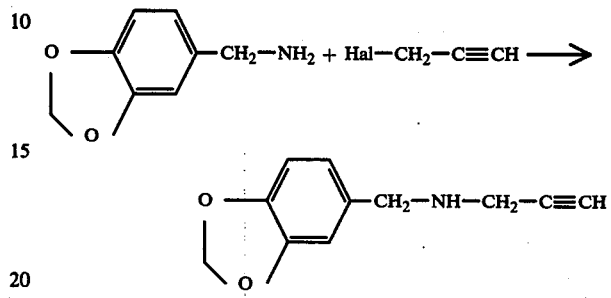

where Hal represents halogen.

The invention also provides a therapeutic composition comprising together with a physiologically acceptable excipient, a pharmaceutically active amount of N-propargyl-piperonylamine or a non-toxic salt thereof.

The following Example illustrates the invention.

EXAMPLE a. 3,4-Methylenedioxybenzyl chloride 153.9 g (1.29 mols) of thionyl chloride are poured onto 65.6 g (0.431 mol) of 3,4-methylenedioxybenzyl alcohol. The mixture is stirred for 90 minutes at ambient temperature (15°–25° C.) and the excess thionyl chloride is then evaporated. The residue is taken up in dimethylformainde (DMF) and the latter is then evaporated. Finally, the residue is taken up in 500 ml of DMF (it is not necessary to isolate the 3,4-methylenedioxybenzyl chloride thus obtained).

b. 3,4-Methylenedioxybenzyl phthalimide 88 g (0.474 mol) of potassium phthalimide are added to the solution of 3,4-methylenedioxybenzyl chloride in DMF obtained in (a), and the mixture is heated for one hours under reflux. It is cooled and the insoluble product is filtered off and washed with distilled water. Thereafter, the insoluble product is dried and the fact that it is 3,4-methylenedioxybenzyl phthalimide is verified.

c. 3,4-Methylenedioxybenzylamine hydrochloride

The phthalimide derivative obtained in (b) is dissolved in 900 ml of 95% ethanol. 24.4 g of hydrazine hydrate are added. The mixture is heated under reflux for 2 hours and then cooled and acidified with concentrated HCl. The insoluble product is filtered off and washed with 4 times 30 ml of 95% strength ethanol. The filtrate is evaporated to dryness, the residue is taken up in distilled water and an insoluble product is filtered off. The aqueous phase is neutralised with sodium hydroxide solution to pH 11 and extracted with ether. The ether is dried over MgSO$_4$ in the presence of 3 SA charcoal, and is filtered. The hydrochloride is precipitated with hydrogen chloride gas. 26 g of 3,4-methylenedioxybenzylamine hydrochloride are obtained.

Yield = 32%

Analysis { % Cl$^-$, measured = 18.85%
         { % Cl$^-$, theoretical = 18.93% d. N-Propargyl-3,4-methylenedioxybenzylamine hydrochloride (alternative nomenclature: N-propargyl-piperonylamine hydrochloride)
Code No. CRL 40,273.

A mixture consisting of 20.8 g (0.138 mol) of 3,4-methylenedioxybenzylamine base (isolated from the hydrochloride obtained above), 8.21 g (0.069 mol) of propargyl bromide, 100 ml of ethanol and 100 ml of pyridine is heated under reflux for 4 hours. It is cooled, insoluble matter is filtered off, the filtrate is evaporated and the residue is taken up in 100 ml of distilled water. The solution is extracted with ether and the ether is dried over $MgSO_4$ in the presence of charcoal (3 SA). The ether is filtered and the hydrochloride is precipitated by bubbling HCl gas through the ether, and is recrystallised from a mixture of acetone and ethanol (50 : 50). 5 g of CRL 40,273 are obtained.
Yield: 33%
Melting point = 200°–210° C.

Analysis $\begin{cases} \% \text{ Cl}^-, \text{ measured} = 15.93\% \\ \% \text{ Cl}^-, \text{ theoretical} = 15.74\% \end{cases}$ The purity is checked by thin layer chromatography [eluant : acetone-methanol (50:50 by volume); plate: silica gel (Merck F 254); development with: U.V. + Draggendorf reagent].

The pharmacological tests undertaken with CRL 40,273 are summarized below.

A. Toxicity

For intravenous administration to mice, the LD-50 of CRL 40,273 is 178 mg/kg and the LD-0 (maximum non-lethal dose) is 160 mg/kg.

B. Anorexia-inducing action

Batches of 8 rats which have been fasting for 48 hours are given gastrically, at time T = O, water or an aqueous solution of CRL 40,273 (the comparison batch is given 5 ml/kg and the other batches are respectively given 32 mg/kg and 128 mg/kg of CRL 40,273 as an aqueous solution, in a volume of 5 ml/kg).

The mean percentage consumption of food and of water up to time T + 24 hours, relative to the comparison batch, is noted. The mean weight of the animals at time T + 24 hours is also noted. It follows from the observations listed in Table I that CRL 40,273 at a dose of 128 mg/kg exerts a marked anorexia-inducing effect of duration greater than 24 hours.

It is also found that the anorexia-inducing effect of CRL 40,273 is close to that of a reference substance, fenfluramine [the systematic nomenclature of which is N-ethyl-α-methyl-m-(trifluoromethyl)phenethylamine] at a dose of 10 mg/kg.

CRL 40,273 does not alter the stereotype behaviour induced by subcutaneous injection of apomorphine (0.5 mg/kg) in rats.

(2) Interaction with amphetamine

Batches of 6 rats are given an intraperitoneal injection of 2 mg/kg of amphetamine 30 minutes after the administration of CRL 40,273. It is found that:
(a) at doses of 4 mg/kg, 16 mg/kg and 64 mg/kg, CRL 40,273 increases the duration and intensity of the amphetamine-induced stereotypies, and
(b) the increase in the duration and intensity of amphetamine-induced stereotypies is much greater at a dose of 16 mg/kg of CRL 40,273 than at doses of 4 mg/kg and 64 mg/kg.

(3) Interaction with reserpine

Four hours after the intraperitoneal administration of 2.5 mg/kg of reserpine, batches of 6 mice are given CRL 40,273; the following is observed:
(a) as regards the temperature, at a dose of 32 mg/kg CRL 40,273 partly opposes the hypothermia induced by reserpine; and
(b) as regards ptosis, CRL 40,273 at a high dose reduces the intensity of the palpebral ptosis caused by reserpine.

(4) Interaction with oxotremorine

Thirty minutes after the intraperitoneal injection of 0.5 mg/kg of oxotremorine into batches of mice, CRL 40,273 is administered; it is found that:
(a) from a dose of 8 mg/kg upwards, this product opposes the hypothermia-inducing action of oxotremorine,
(b) it does not modify the intensity of the tremors provoked by oxotremorine and
(c) it does not modify the cholinergic peripheral stimulation phenomena (salivation, lachrymation and defaecation).

(5) Effect on the four plate test, traction and electrical shock

CRL administered to batches of 10 sensitive mice (EVIC CEBA), 30 minutes before the test, does not produce an increase in the number of incorrect moves which are punished, does not bring about any major incapacity and does not modify the convulsing effects of the electrical shock.

(6) Effect on the motility
(a) Spontaneous motility

The mice receive the CRL 40,273 30 minutes before being placed in the actimeters, where their motility is recorded for 30 minutes (6 mice per dose, 12 comparison animals). Below 32 mg/kg the CRL has no effect on the spontaneous locomotor activity of the mouse. It is from a dose of 32 mg/kg upwards that hypomotility

TABLE I

| Product | Dose | Mean weight of the rats | | Percentage consumption | | | | | | | |
|---|---|---|---|---|---|---|---|---|---|---|---|
| | | | | Food | | | | | Wate | | |
| | | T=O | T+24hrs | T+1hr | T+3hrs | T+5hrs | T+7hrs | T+24hrs | T+5hr | T+7hrs | T+24hrs |
| Water | 5 ml/kg | 244 g | 257 g | 100% | 100% | 100% | 100% | 100% | 100% | 100% | 100% |
| CRL 40,273 | 32 mg/kg | 243 g | 260 g | 82% | 89% | 100% | 98% | 99% | 132% | 135% | 94% |
| | 128 mg/kg | 240 g | 227 g | 35% | 37% | 33% | 36% | 30% | 63% | 65% | 39% |

C. Action on the central nervous system

In the experiments shown below, CRL 40,273 was administered intraperitoneally as a suspension in an aqueous solution of gum arabic, in a volume of 20 ml/kg in the case of mice and of 5 ml/kg in the case of rats.
(1) Interaction with apomorphine manifests itself; at a dose of 128 mg/kg the hypomotility is marked.

(b) Motility reduced by habituation to the cage (residual motility)

After remaining for 18 hours in the actimeters, the mice (6 per dose, 12 comparison animals) receive CRL 40,273 and are immediately replaced in their cages, and half an hour afterwards the recording of the motility starts and is continued for 30 minutes. At doses of 0.5 mg/kg and 1 mg/kg of CRL 40,273 a renewal of activity in mice habituated to their cage is found.

(c) Motility reduced by hypoxia treatment 30 minutes after administration of CRL 40,273 the mice (10 per dose, 20 comparison animals) are subjected to anoxia by pressure reduction (depression of 600 mm Hg in 90 seconds, returned to normal pressure in 45 seconds), and are then placed in the actimeters where their motility is noted for 10 minutes. It is observed that CRL 40,273 does not produce an improvement in the motor recovery of mice of which the motility has been reduced by anoxia induced by pressure reduction.

(7) Effect on inter-group aggressiveness

After 3 weeks' residence in each of the halves of a cage divided by an opaque partition, groups of three mice receive CRL 40,273 30 minutes before being brought together by withdrawing the partition, and the number of fights which take place in the course of the following 15 minutes is noted. It is found that:

(a) at doses of 0.5 mg/kg, 1 mg/kg and 2 mg/kg, CRL 40,273 moderately reduces the aggressiveness;

(b) at a dose of 4 mg/kg and (to a lesser degree) at a dose of 8 mg/kg the results are difficult to record as the antiaggressive action of CRL 40,273 becomes more pronounced; and (c) at doses of 16 mg/kg, 32 mg/kg and 64 mg/kg, CRL 40,273 completely inhibits the aggressive behaviour.

It follows from all these tests on the central nervous system that CRL 40,273 is a substance which acts on the central nervous system and which is useful as an anorexia-inducing agent for reducing the appetite. Alongside the anorexia-inducing property, CRL 40,273 exhibits:

firstly, the profile of a weak anti-depressant (characterized by mydriasis, by antagonism to reserpine and to oxotremorine, and by boosting of amphetamine-induced stereotypies) and secondly, a depressive activity on the inter-group aggressiveness of mice at doses which do not produce a depression of the motility but which, paradoxically, bring about an increase of the aggressiveness reaction to an object manipulated by the experimenter.

As regards the question of aggressiveness, it is assumed that CRL 40,273 reduces a certain form of aggressiveness which would develop in the absence of stimulation and brings about an increase in the "reaction" aggressiveness which would only take place after a primary aggression.

D. Cardiovascular action

The study of the cardiovascular action was carried out on rats and on dogs. It was completed by investigating possible interactions with substances which act on the central nervous system, in respect of the hypotensive properties.

(1) Test on rats

In rats suffering from spontaneous hypertension, CRL 40,273, administered orally, has a hypotensive action from a dose of 16 mg/kg upwards. In effect, it is found that:

(a) below this dose and, it particular, at a dose of 5 mg/kg (5animals), the arterial pressure (150 mm Hg) and the pulse rate (430 beats/minute) remain unaltered for the duration of the experiment (6 hours);

(b) at a dose of 16 mg/kg (9 animals), the arterial pressure begins to decrease 2 hours after the administration of CRL 40,273, reaching its minimum level ($-16\%$, a statistically significant decrease) 4 hours after administration, and remains at this level for the next 3 hours, and the pulse rate decreases ($-12\%$, a statistically significant decrease) and does not rise again during the next 6 hours;

(c) at a dose of 32 mg/kg (six animals), the arterial pressure decreases immediately after administration, reaching its minimum level ($-18\%$, a statistically significant decrease) 4 hours after the said administration, and remains at this level for the next 2 hours, and the pulse rate decreases immediately after administration, reaching its minimum level ($-16\%$, a statistically significant decrease) after 1 hour, and remaining thereat for 1 hour before risng gradually.

(2) Tests on dogs

In dogs anaesthetised with Nembutal, CRL 40,273, administered intravenously at doses of 2 mg/kg, 4 mg/kg, 8 mg/kg and 16 mg/kg, exhibits no clear cardiovascular action, however, except, for an increase in the flow rate of the femoral artery from a dose of 4 mg/kg upwards.

(3) Interaction with other substances acting on the central nervous system

The preceding two types of tests show that CRL 40,273 is an agent of the anti-hypertensive type and supplementary tests were therefore carried out with depressants and neuroleptic agents.

(a) Interaction with depressants

In rats it is found, after intraperitoneal administration, that CRL 40,273 boosts the motor incoordination induced by Diazepam and ethanol, whilst the myorelaxing effects of these substances are only slightly increased.

(b) Interaction with neuroleptic agents

In rats it is found, after intraperitoneal administration, that the hypotensive effect of CRL 40,273 appears to be boosted by Levomepromazine, that the simultaneous effect of CRL 40,273 and of Chlorpromazine appears to prolong the hypotension due to Chlorpromazine without, however, reaching lower figures then those obtained with Chlorpromazine alone and that the combination of CRL 40,273 with Haloperidol has no effect on the arterial pressure and slightly lowers the pulse rate.

E. Conclusions and indications

The totality of the tests summarised above shows that CRL 40,273, which has three different types of action, namely on anorexigenic action, a specific action on the central nervous system and a hypotensive action, can be used as a medicament for three distinct indications, namely, reduction of appetite, anti-fatigue treatment and treatment of aggressiveness.

In man, CRL 40,273 has given good results as an anti-fatigue and anti-aggression medicament, after administration by injection and after oral administration. It has in particular been employed in the form of injectable ampoules each containing 40 mg of active principle dissolved in an isotonic solution, at the rate of 2 to 3 ampoules per day, and in the form of tablets each containing 100 mg of active principle, at the rate of 1 to 2 tablets per day.

Some clinical observations have been given below.

OBSERVATION A

Mr. Ali B . . ., 28 years old, living in France for 6 years, an unskilled labourer, single, presents himself at the emergency department of hospital X . . . for the purpose of being hospitalized. This patient presents himself as being highly vindictive, and hides severe aggressiveness behind an apparent calm. The interviewer learns that over the course of 2 years the patient has been hospitalized almost 10 times at the psychiatric hospital in Z . . .

The clinical examination of the patient, and especially the neurological examination, is strictly normal. The only functional sign is a vague giddiness which the patient describes vehemently. Pulse rate = 84 beats/minute, and arterial pressure (AP) = 12/7 cm Hg.

Overall, these are symptoms of the hypochondriac type. As time passes, the allegations of the patient regarding his condition increase and an obvious aggressiveness evolves. The patient directs threats and insults at the medical personnel.

He is given, not without pessimism, an intramuscular injection of CRL 40,273 and the following reactions are noted:

(1) 15 minutes after the injection

The patient is immediately relaxed and congratulates the physician, is this a "placebo relaxation" or a real effect of the medicament?

there is no change in alertness, and the pulse and arterial pressure are unchanged.

(2) 30 minutes after the injection

The patient has genuinely lost all aggressiveness, and the pulse arterial pressure and alertness are normal.

(3) An ECG carried out 1 hour after the injection shows no abnormalities, no disturbances of the rhythm, and no depolarization or repolarization disturbances. The pulse and arterial pressure remain unchanged.

The patient leaves with a treatment based on minor tranquillizers and asks to be seen again in specialist consultation.

OBSERVATION B

Mr. Rene C . . ., 29 years old, single, arrives at the emergency department of hospital X . . ., brought by a group of friends. It is learnt that he has been a post-traumatic epileptic for 5 years.

Clinical examination shows a pulse rate of 82 beats/minute, an arterial pressure of 13/8 cm Hg, an obvious (+++) psychomotor agitation and aggressiveness towards his friends and the hospital personnel.

The patient accepts, without problems, the intramuscular administration of an ampoule of CRL 40,273. Behind his agitation is observed a depressive trait relating to his illness — he is treated with GARDENAL (50 mg in the morning, 100 mg in the evening). The last crisis occurred 3 weeks previously.

(1) 15 minutes after the injection, the following are noted

Sedation of the psychomotor agitation, the patient sits on the edge of the bed and has obviously lost all psychomotor symptoms, logorrhoeic symptoms have disappeared and the patient becomes silent, agitation symptoms have disappeared and the patient becomes apragmatical and somnolent, and the pulse and arterial pressure remain the same.

(2) 30 minutes after the injection, the following are noted

Alertness has returned to normal, there is an almost complete loss of aggressiveness but the patient nevertheless refuses hospitalization, and the ECG shows no abnormalities.

(3) 1 hour later

The pulse is 82 beats/minute and the arterial pressure is 13/8 cm Hg, and the patient is self-critical, leaves satisfied and asks to return for a neurological consultation.

OBSERVATION C

Mr. Philippe B . . ., single, 35 years old, arrives at the emergency department of hospital X . . ., brought by first-aid police after falling in the road.

On arrival, clinical examination shows:

the absence of enolic impregnation, a calm stage 1 coma, froth on the lips, a pulse of 80 beats/minute and an arterial pressure of 14/8 cm Hg, and previous comitial crises, the first crisis 11 years ago.

The patient is sent to the surgical department for X-rays of the knees because ecchymoses have been noted.

Thirty minutes later, the patient returns to the emergency department unaided, conscious and obviously very agitated. He offers threats, and grabs the telephone, which he seeks to tear out and break. He exhibits obvious aggressiveness towards the nursing personnel.

The patient is immobilized and is given an intramuscular injection of CRL 40,273.

(1) 5 minutes after the injection, the following are noted

A reduction in alertness — the patient exhibits obnubilation and utters incomprehensible phrases, and the pulse has slowed down to 64 beats/minute, the arterial pressure being 14/8 cm Hg.

(2) At the end of 20 minutes after the injection

The patient is again conscious and is in the grip of a true delirious outburst — he thinks himself a Canadian secret agent.

he is intensely hilarious, the pulse and arterial pressure are unchanged and an ECG carried out shows no abnormality.

(3) After 1 hour

The psychomotor agitation has returned, but without aggressiveness.

OBSERVATION D

Mrs. Martine L . . ., 56 years old, menopausal for 4 years, married and mother of two children, arrives at the emergency department, brought by first-aid police, in a state of manic agitation. On all the evidence, this patient exhibits psychomotor agitation; she howls, wants to break everything and grabs a chair in order to break the equipment in the room. She is akathisic. She thanks the hospital personnel and inveighs against her family.

Any clinical examination is virtually impossible and and as a first stage the patient is isolated; her agitation increases and she becomes aggressive towards the hospital personnel.

After having struggled, the patient is given an intramuscular injection of CRL 40,273.

(1) 15 minutes after the injection, the following are noted

The agitation is followed by a crisis of tears, there is more howling, pulse = 72 beats/minute and arterial pressure = 11/7 cm Hg.

The patient sits on the edge of the bed and her thoughts appear elsewhere. Total apragmatism is observed.

(2) 30 minutes after the injection

It is noted that this phase of apragmatism is followed by euphoria, a laughing crisis and puerilism.

Alertness is normal and pyschomotor agitation nil. The pulse and arterial pressure remain unchanged.

Cardiac auscultation does not allow any disturbance of the rhythm, or extrasystoles, to be observed.

(3) 1 hour after the injection

The patient is relaxed, calm and serene, speaks with humour (an infantile humour) and accepts her hospitalization.

I claim:

1. A pharmaceutical composition useful in the treatment of aggression comprising an anti-aggression effective amount of N-propargyl-piperonylamine or a non-toxic addition salt thereof in combination with a physiologically acceptable excipient.

2. A method of reducing aggression which comprises administering to a patient an anti-aggression effective amount of N-propargylpiperonylamine or a non-toxic addition salt thereof.

* * * * *